US00PP12059P2

(12) United States Plant Patent
VandenBerg

(10) Patent No.: US PP12,059 P2
(45) Date of Patent: Aug. 14, 2001

(54) CHRYSANTHEMUM PLANT NAMED 'YELLOW SPOKANE'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/383,531

(22) Filed: Aug. 26, 1999

(51) Int. Cl.[7] ..... A01H 5/00
(52) U.S. Cl. ..... Plt./289
(58) Field of Search ..... Plt./289, 295

(56) References Cited

U.S. PATENT DOCUMENTS 4,616,099 * 10/1986 Sparkes ..... 47/58

OTHER PUBLICATIONS

Chan, 1996, "Chrysanthemum and rose mutations induced by x–rays", Am. Soc. Hort. Sci. Proc., pp. 613–620.*
Broertjes, 1966, "Mutation breeding of chrysanthemums", Euphytica, 15:156–162.*
Dowrick, et al., 1966, "The induction of mutations in Chrysanthemum using x–and gamma radiation", Euphytica, 15:204–210.*
Broertjes, et al., 1980, A mutant of a mutant of a mutant of a . . . Irradiation of progressive radiation–induced mutants in a mutation breeding programme with *Chrysanthemum morifolium*, Euphytica 29:525–530.*
Gosling, ed., 1979, The Chrysanthemum Manual—6$^{th}$ edition, The National Chrysanthemum Society, London, Essex Telegraph Press, Ltd., pp. 329–336.*
Broertjes, et al., 1978, "Application of Mutation Breeding Methods in the Improvement of Vegetatively Propagated Crops", Elsevier Sci. Pub. Co., New York, pp. 162–175.*
Searle, et al., 1968, "Chrysanthemums the Year Round", Blanford Press, London, pp. 27–29, 320–327.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yellow Spokane', characterized by its large decorative quilled-type inflorescences that are about 8.3 cm in diameter; attractive yellow ray florets; freely flowering; early flowering, response time is about 52 days; dark green foliage; strong stems; and good postproduction longevity with inflorescences maintaining good substance and color for about three weeks in an interior environment.

3 Drawing Sheets

BACKGROUND OF THE INVENTION

The present invention relates to a new and distinct cultivar of Chrysanthemum plant, botanically known as *Dendranthema grandiflora* and referred to by the cultivar name Yellow Spokane.

The new Chrysanthemum is a product of a mutation induction breeding program conducted by the Inventor in Fort Myers, Fla., and Salinas, Calif. The objective of the program is to create new Chrysanthemum cultivars with desirable inflorescences form and floret colors, good substance, and good postproduction longevity.

The new Chrysanthemum originated by exposing uprooted cuttings of the Chrysanthemum cultivar Spokane, disclosed in U.S. Plant Pat. No. 10,604, to X-ray radiation at a level of 2,000 rads on Aug. 3, 1995, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemum was discovered and selected by the Inventor as a single flowering plant within this population in March, 1996. The selection of this plant was based on its desirable inflorescence form and floret colors and good postproduction longevity.

Asexual reproduction of the new Chrysanthemum by terminal cuttings taken in a controlled environment in Alva, Fla., has shown that the unique features of this new Chrysanthemum are stable and reproduced true to type in successive generations.

SUMMARY OF THE INVENTION

The cultivar Yellow Spokane has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yellow Spokane'. These characteristics in combination distinguish 'Yellow Spokane' as a new and distinct cultivar:

1. Large quilled decorative-type inflorescences that are about 8.3 cm in diameter.
2. Attractive yellow ray florets.
3. Freely flowering.
4. Early flowering, response time is about 52 days.
5. Dark green foliage.
6. Strong stems.
7. Good postproduction longevity with inflorescences maintaining good substance and color for about three weeks in an interior environment.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type.

The photograph on the first sheet comprises a side perspective view of a typical flowering stem of 'Yellow Spokane' grown as a spray-type cut Chrysanthemum.

The photograph on the second sheet comprises a top perspective view of typical inflorescences of the cultivar Yellow Spokane.

The photograph at the top of the third sheet comprises a close-up view of upper and lower surfaces of typical inflorescences of the cultivar Yellow Spokane.

The photograph at the bottom of the third sheet comprises a close-up view of typical young and mature leaves of the cultivar Yellow Spokane. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate commercial practice in a double-layer polyethylene-covered greenhouse. Two-week old rooted cuttings were planted on Feb. 4, 1999 and received 14 long day/short nights followed by short day/long nights until flowering. Plants were grown as single-stem cut Chrysanthemums. During the production time, the following environmental conditions were measured: day temperatures ranging from 18 to 27° C.; night temperatures ranging from 16 to 18° C.; and light level of about 2,000 to 4,000 foot-candles. Measurements and numerical values represent averages for six to ten typical flowering stems.

Botanical classification: *Dendranthema grandiflora* cultivar Yellow Spokane.

Commercial classification: Decorative quilled spray-type cut Chrysanthemum with tubular ray florets.

Parentage: Induced mutation of *Dendranthema grandiflora* cultivar Spokane, disclosed in U.S. Plant Pat. No. 10,604.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative quilled spray-type cut flower. Stems upright, uniform habit and freely branching.

*Flowering stem length.*—About 68.5 cm.

*Stem color.*—144A.

*Foliage description.*—Arrangement: Alternate. Length: About 9.6 cm. Width: About 6.1 cm. Apex: Mucronate. Base: Truncate to attenuate. Margin: Palmately lobed. Texture: Upper and lower surfaces slightly pubescent. Veins prominent on lower surface. Color: Young and mature foliage upper surface: 147A. Young and mature foliage lower surface: 147B. Venation upper surface: 147B. Venation lower surface: 147C. Petiole: Length: About 3.1 cm. Diameter: About 3 mm. Color: Upper, 147C; lower, 147C; margins, 147A.

Flowering description:

*Appearance.*—Decorative quill spray-type inflorescence form with oblong-shaped ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 52 days later.

*Postproduction longevity.*—In an interior environment, flowering stems will maintain good color and substance for about three weeks in an interior environment after one week of cool storage.

*Quantity of inflorescences.*—About 12 inflorescences per flowering stem.

*Inflorescence size.*—Diameter: About 8.3 cm. Depth (height): About 2.5 cm. Diameter of disc: No disc florets observed. Diameter of receptacle: About 7 mm.

*Ray florets.*—Shape: Tubular, quilled. Length: About 4.7 cm. Width: Narrow, about 3 mm. Apex: Acute to dentate. Base: Fused. Margin: Tubular. Texture: Very smooth, glabrous; durable. Aspect: Initially upright, then perpendicular to peduncle; incurved. Number of ray florets per inflorescence: Numerous, full inflorescences, typically more than 200. Color: When opening: Apex, 7A; base, 5A to 4A-4B. Mature, tube: Apex, 7A; midsection and base, 4C to mostly 4D. Mature, throat: 7A to 5A to 4A.

*Peduncle.*—Aspect: Strong, angled about 55° to the stem. Length: First peduncle: About 6.6 cm. Third peduncle: About 12 cm. Seventh peduncle: About 15.3 cm. Texture: Very fine pubescence. Color: 144A.

*Reproductive organs.*—Androecium: None, no disc florets observed. Gynoecium: Present on ray florets.

Disease resistance: Resistance to diseases common to Chrysanthemums has not been observed on plants grown under commercial conditions.

Temperature tolerance: Plants of the new Chrysanthemum have demonstrated good tolerance to temperatures as low as 5° C.

Seed production: Seed production has not been observed.

It is claimed:

1. A new and distinct cultivar of Chrysanthemum plant named 'Yellow Spokane', as illustrated and described.

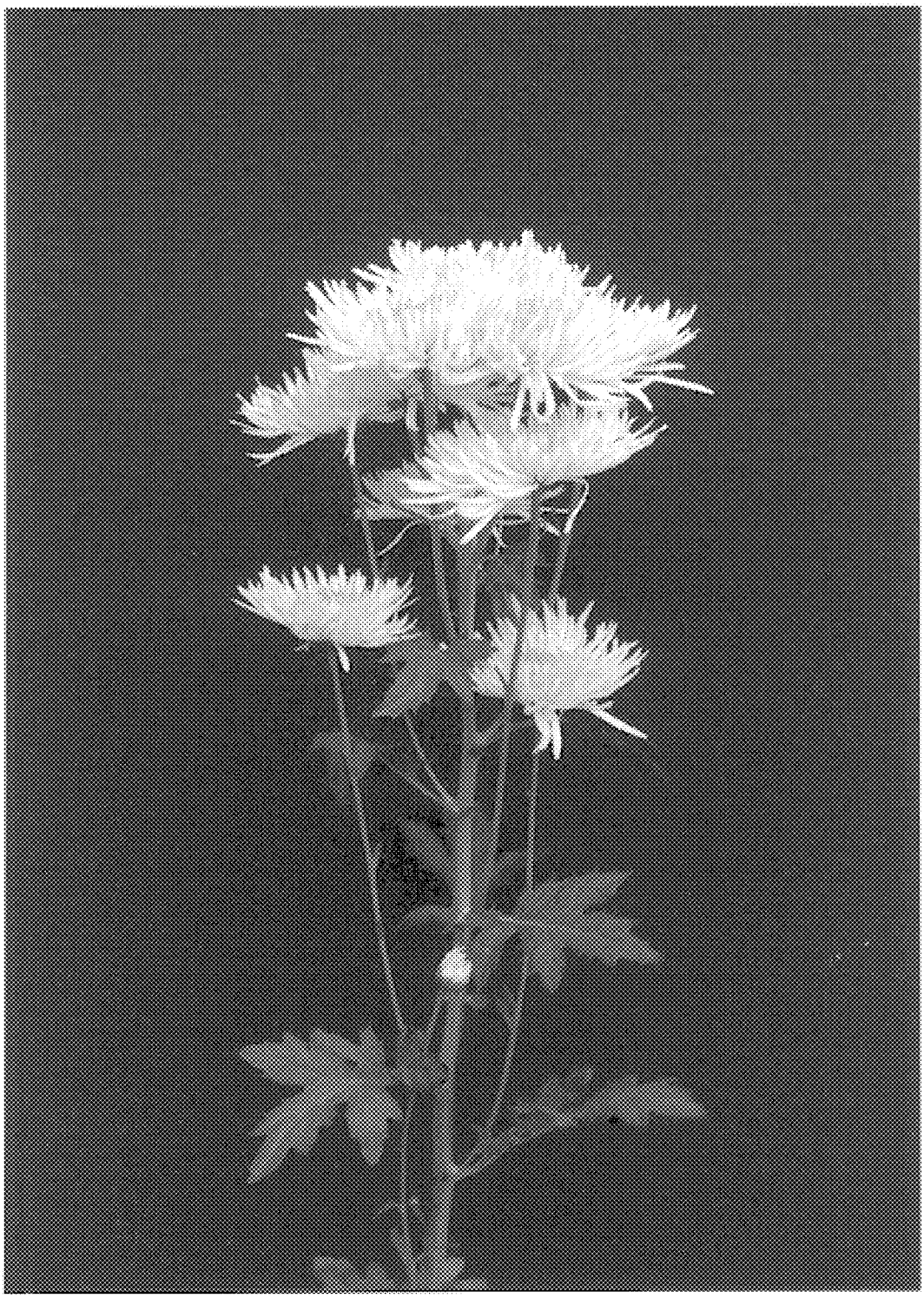

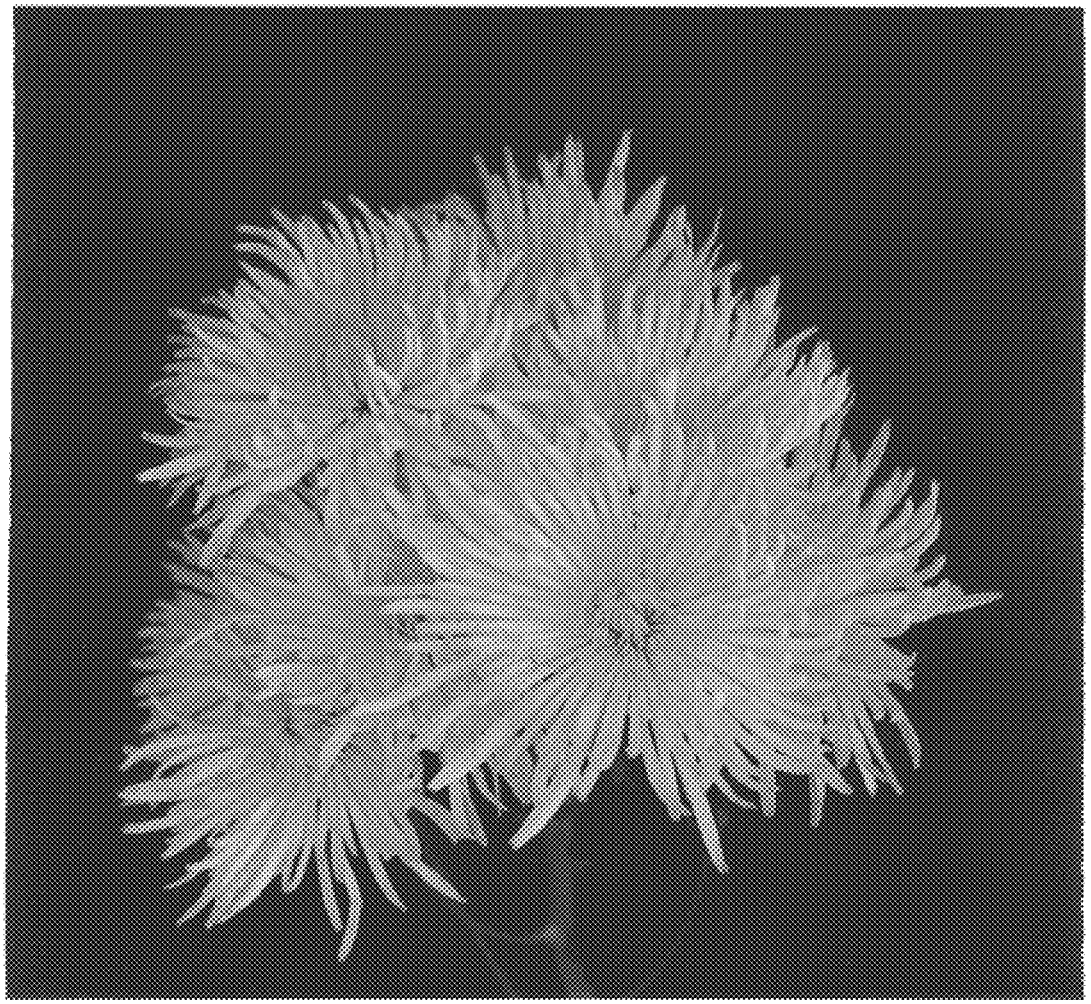

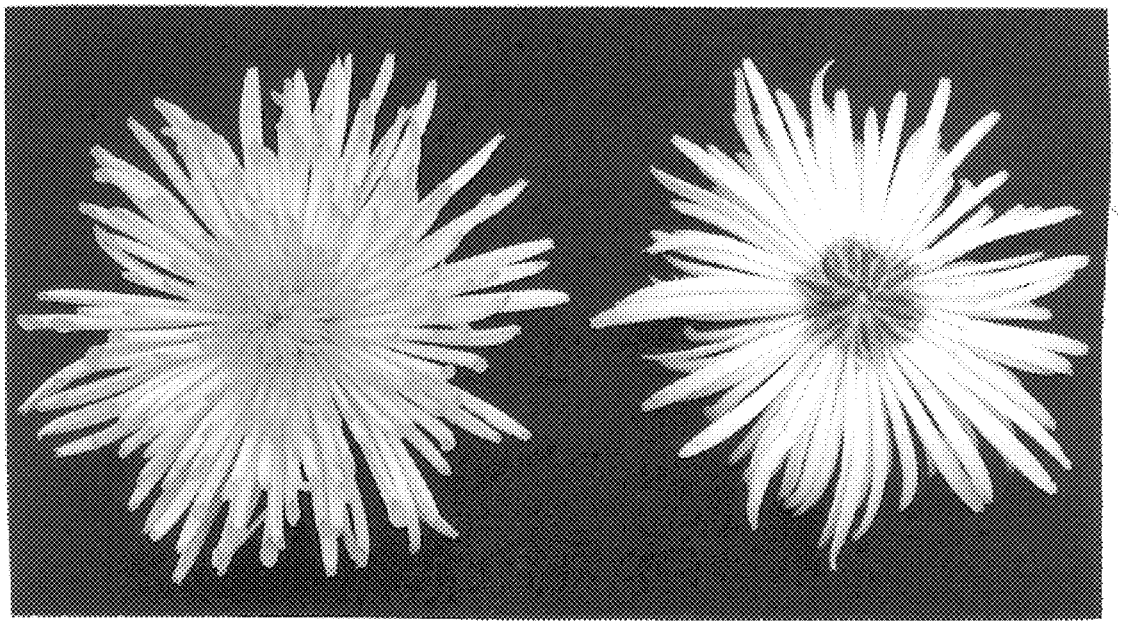
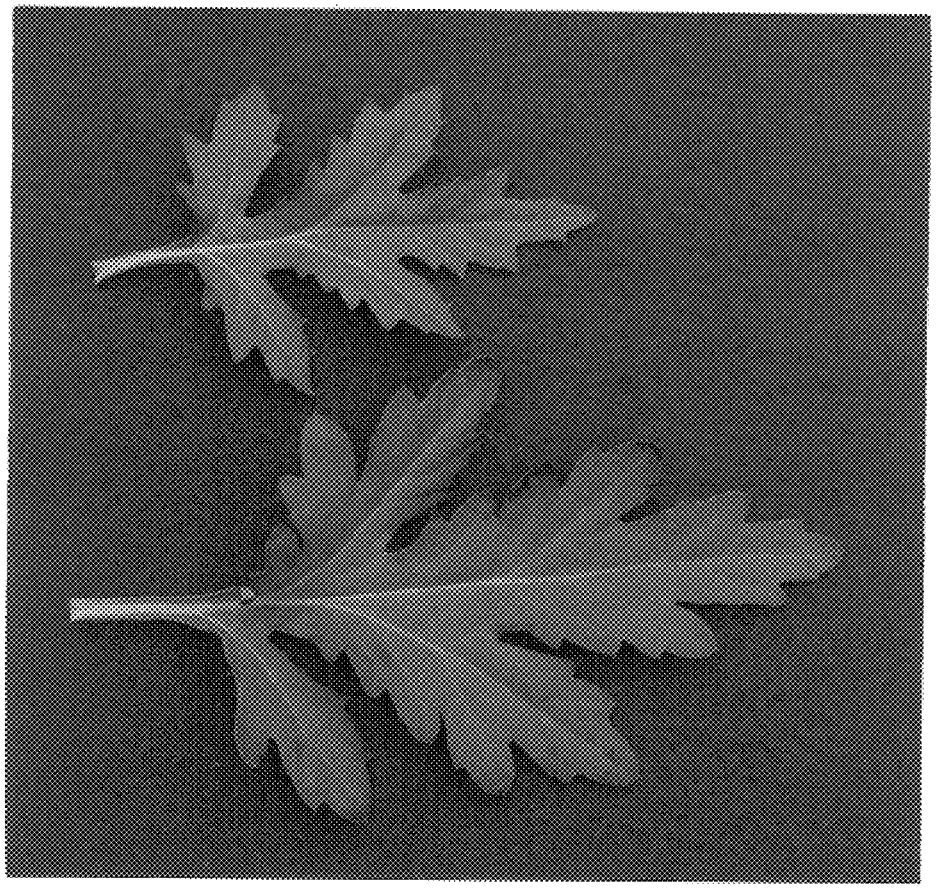

* * * * *